United States Patent [19]
Levis

[11] Patent Number: 5,547,461
[45] Date of Patent: Aug. 20, 1996

[54] INFLATABLE LUMBAR SUPPORT FOR BACKPACK

[75] Inventor: Jeffrey D. Levis, Fresno, Calif.

[73] Assignee: Mountain Equipment, Inc., Fresno, Calif.

[21] Appl. No.: 343,330

[22] Filed: Nov. 21, 1994

[51] Int. Cl.⁶ .............................. A61F 5/00; A61F 5/37; A45F 3/04
[52] U.S. Cl. .............................. 602/19; 128/876; 602/13; 5/634
[58] Field of Search .................................. 128/869, 874, 128/875, 876, DIG. 20; 602/13, 19; 224/209, 210, 211, 215; 2/69.5, 94, 69

[56] References Cited

U.S. PATENT DOCUMENTS

| | | | |
|---|---|---|---|
| 3,071,133 | 1/1963 | Eisen | 602/13 |
| 3,521,623 | 7/1970 | Nichols | 602/13 |
| 3,667,457 | 6/1972 | Zumaglini | 602/19 |
| 3,679,108 | 7/1972 | Ingram | 224/209 |
| 3,902,640 | 1/1975 | Geiben | 224/215 |
| 4,135,503 | 1/1979 | Romano . | |
| 4,559,933 | 12/1985 | Batard | 602/13 |
| 4,681,113 | 7/1987 | Coplans . | |
| 4,682,587 | 7/1987 | Curlee . | |
| 4,682,588 | 7/1987 | Curlee . | |
| 4,744,398 | 5/1988 | Clark | 224/209 |
| 4,789,202 | 4/1988 | Alter . | |
| 4,993,409 | 1/1991 | Grim . | |
| 5,016,620 | 5/1991 | Matthews | 602/19 |
| 5,195,948 | 3/1993 | Hill | 602/19 |
| 5,205,814 | 4/1993 | Lundrigan et al. . | |
| 5,378,224 | 1/1995 | Billotti | 602/13 |

Primary Examiner—Michael A. Brown
Attorney, Agent, or Firm—Mark D. Miller

[57] ABSTRACT

A removable inflatable support and comfort bag that is designed to be inserted into a specially formed pocket built into the lumbar region of a backpack waist belt. The partially or fully inflated bag helps transfer the weight of the load of the backpack in the lumbar region of the user's back, providing relief from fatigue. The bag is in the form of an airtight, watertight bladder that is insertable into a lumbar pocket in the waist belt of a backpack, and is connected by a hose to a hand pump which includes a release valve. The waist belt may include a pre-molded pad with grooves for channeling perspiration and moisture away from the lumbar region.

20 Claims, 4 Drawing Sheets

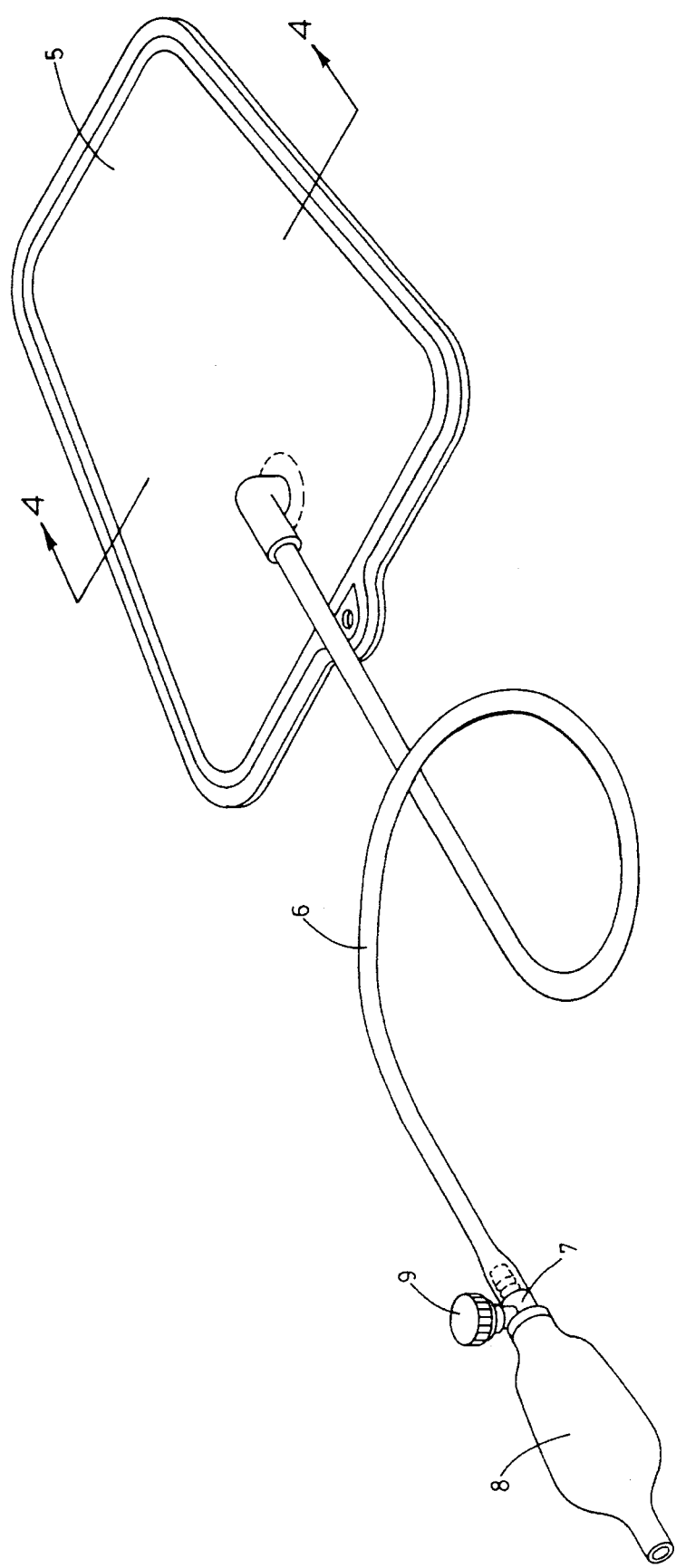
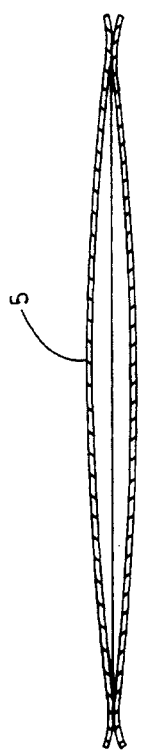
FIG. 3
FIG. 4

INFLATABLE LUMBAR SUPPORT FOR BACKPACK

BACKGROUND OF THE INVENTION

The present invention relates to packs used in outdoor backpacking, and more particularly to a new and improved lumbar support and comfort device for a backpack.

Backpacking has become a popular all-season outdoor recreational activity. Overnight backpacking camping trips and extended cold-weather day trips usually require large capacity packs. The larger and heavier the pack, the more important even load distribution becomes. Padded waist belts are designed to transfer the bulk of the weight of the pack to the pelvis area of the user. Shoulder straps transfer the remaining weight to the user's back, and are used to adjust the pack to distribute the load between the user's back and pelvis area.

Over many hours or many days of use, it is common for a backpacker to develop fatigue in the lower lumbar region of the back. This is particularly true if an excessive load is inadvertently or deliberately placed on the shoulders and back instead of the waist. Such constant weight on the shoulders and back is absorbed by the vertebrae of the spine where fatigue can then develop. Such fatigue can be increased by poor posture of the user while wearing the backpack.

SUMMARY OF THE INVENTION

The present invention solves many of the support and fatigue problems presented by heavy backpacks by providing a removable inflatable support and comfort bag that is designed to be inserted into a specially formed pocket built into the lumbar region of a backpack waist belt. The partially or fully inflated bag helps transfer the weight of the load of the backpack in the lumbar region of the back, providing relief from fatigue. The bag is in the form of an airtight, watertight bladder connected by a hose to a hand pump which includes a release valve. The pocket is located in a pad that may be folded into place in the lumbar region of the waist belt. In an alternative embodiment, the pad includes a pre-molded pattern for improved comfort. The pattern is designed to facilitate more rapid removal of perspiration and moisture from the lumbar region.

The pocket in the backpack may be closable by means of a zipper, interengaging hook and loop means (Velcro®), snaps, buttons, or the like which allow the hose to extend out therefrom. The pump may be a squeeze bulb or other hand operated inflation device. The bag is inserted into the pocket, and partially or fully inflated using the hand pump until the appropriate relief from the load is achieved. If relief is needed in a particular area of the lumbar region, the bag may be shifted to that area and partially or fully inflated to provide maximum comfort. If no additional support or comfort is required, the bag can be deflated and/or removed.

It is therefore a primary object of the present invention to provide a removable, inflatable support and comfort device that is insertable into a pocket of the waist belt of a backpack to provide the wearer with relief from fatigue in the lumbar region of the back.

It is a further important object of the present invention to provide a removable, adjustable device to provide support and comfort in the lumbar region of a backpack waist belt.

It is a further object of the present invention to provide a removable support and comfort bag for use in a pocket of the waist belt of a backpack that may be moved around within such pocket to provide relief from fatigue to a targeted area.

It is a further object of the present invention to provide a pocket in the waist belt of a backpack for receiving a partially or fully inflatable support and comfort device to help shift the weight of the backpack in the lumbar region of the user's back.

It is a further object of the present invention to provide a device that gives relief from fatigue in the lumbar region of the back caused by the load of a backpack.

It is a further object of the present invention to provide the combination of an inflatable bag connected to a hose, hand pump and valve together with a pocket in the waist belt of a backpack for receiving said bag to provide adjustment of the backpack while being worn to move the in from the lumbar region of the wearer's back thereby providing relief from fatigue. It is a further object of the present invention to provide a pocket located in a pad that may be folded into the lumbar region of the waist belt of a backpack, said pocket receiving a partially or fully inflatable support and comfort device to help shift the weight of the backpack in the lumbar region of the user's back.

It is a further object of the present invention to provide a pre-molded pad that may be folded into the lumbar region of the waist belt of a backpack, said pad including a pocket for receiving a partially or fully inflatable support and comfort device to help shift the weight of the backpack in the lumbar region of the user's back.

BRIEF DESCRIPTION OF THE DRAWINGS

FIG. 3 is a perspective view of the inflatable bag, hose, valve and hand pump of the present invention separate and removed from the pocket of the backpack.

FIG. 4 is a cutaway side view of the inflatable bag of the present invention along line 4—4 of FIG. 3.

DETAILED DESCRIPTION OF THE DRAWINGS

Figure 1:
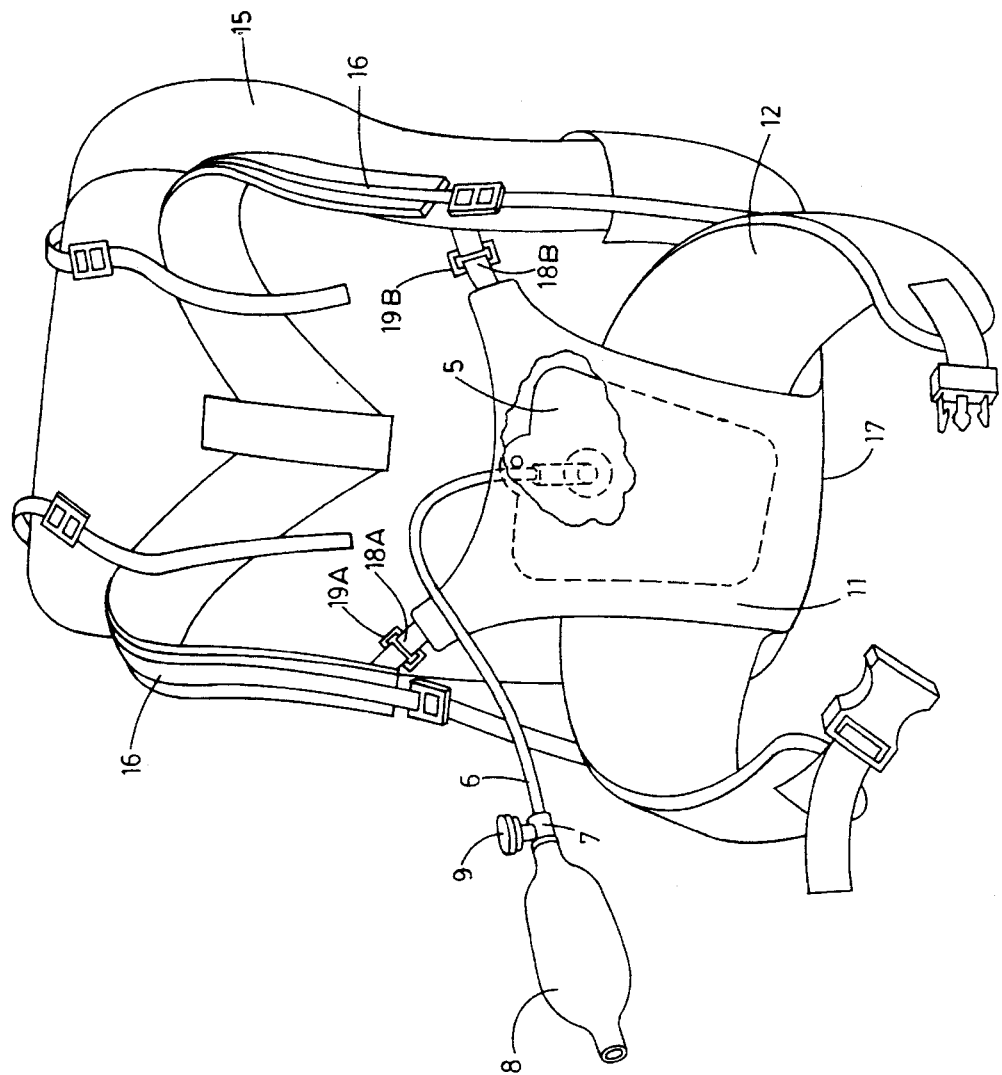
FIG. 1 is a perspective partially cut-away view of the inflatable bag of the present invention inserted into the pocket of the waist belt of a backpack and attached to a hose, valve and hand pump. The pocket of the waist belt is shown in a folded, engaged position.
Figure 2:
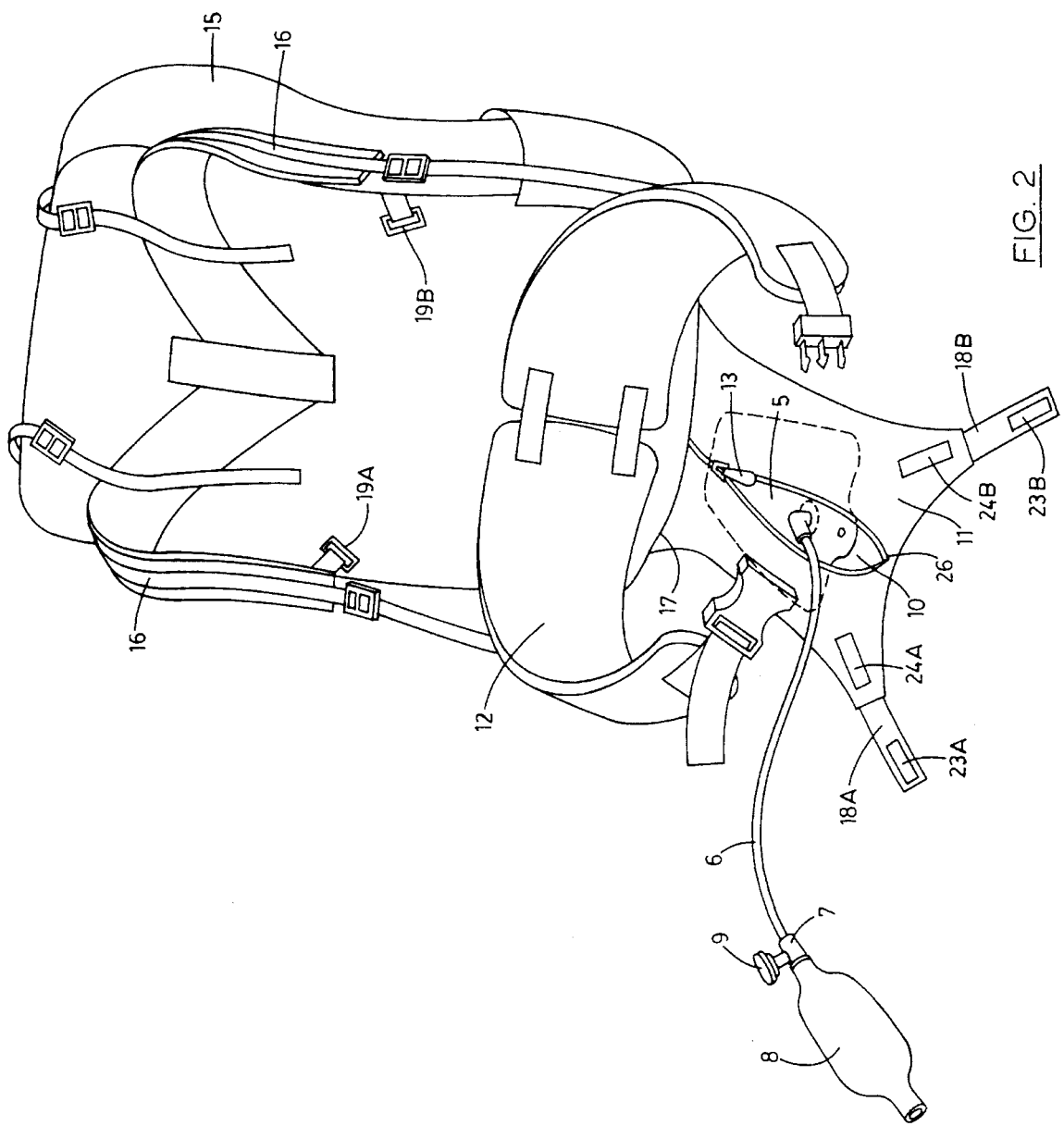
FIG. 2 is a perspective partially cut-away view of the present invention showing the pocket of the waist belt in disengaged position and showing the method of insertion of the bag into the pocket.

Referring to the drawings wherein like reference characters designate like or corresponding parts throughout the several views, and referring particularly to FIGS. 1, 2 and 3, it is seen that the invention includes an inflatable bag 5 attached to a hose 6 at one end, and a valve 7 and hand pump 8 at the other end. The bag is insertable into a pocket 10 in a foldable pad section 11 of the backpack waist belt 12. Pad section 11 is foldable along line 17 as shown in FIG. 2. The pocket is closable using a means 13 such as a zipper or other suitable closing means. Pad section 11 containing pocket 10 includes a pair of straps 18a and 18b attached to the corners opposite fold 17. A pair of buckle means 19a and 19b are located on backpack 15 above waist belt 12. After pocket 10 is closed (whether or not bag 5 is inserted therein), pad section 11 may be folded upward along fold 17 and attached to buckles 19a and 19b using, respectively, straps 18a and 18b (see FIG. 1). This places the pad section 11 between the user and the waist belt 12.

Each of straps 18a and 18b include interengaging means 23a and 23b (such as Velcro®) which engage with corresponding interengaging means 24a and 24b, respectively, located on the surface of pad section 11 (see FIG. 2).

When the pocket is closed as shown in FIG. 1, hose 6 protrudes through the end 26 of zipper 13 to the outside. The hose 6 is long enough to allow easy access by the backpack wearer so that hand pump 8 and the clamp 9 of valve 7 may be easily operated.

In use, bag 5 is inserted into the pocket section 11 of waist belt 12 as shown in FIG. 2. Section 11 is then folded inside waist belt 12 so that it corresponds to the lumbar region of the back of the wearer when in use (see FIG. 1). The backpack 15 is then donned by the wearer with shoulder straps 16 over the wearer's shoulders, and waist belt 12 wrapped around the waist. The weight of the backpack is thereby transferred to the waist, back and shoulders of the user. In order to move the weight of the backpack in the lumbar region of the wearer's back, bag 5 of the present invention may be partially or completely inflated using hand pump 8. Air may be adjustably released from the bag by turning clamp 9 of valve 7 until a proper level of comfort is reached.

Pocket 10 is large enough that bag 5 may be moved around therein in order to target relief to a particular area of the lumbar region of the wearer. Bag 5 may also be removed entirely (see FIG. 3) from pocket 10.

Figure 5:
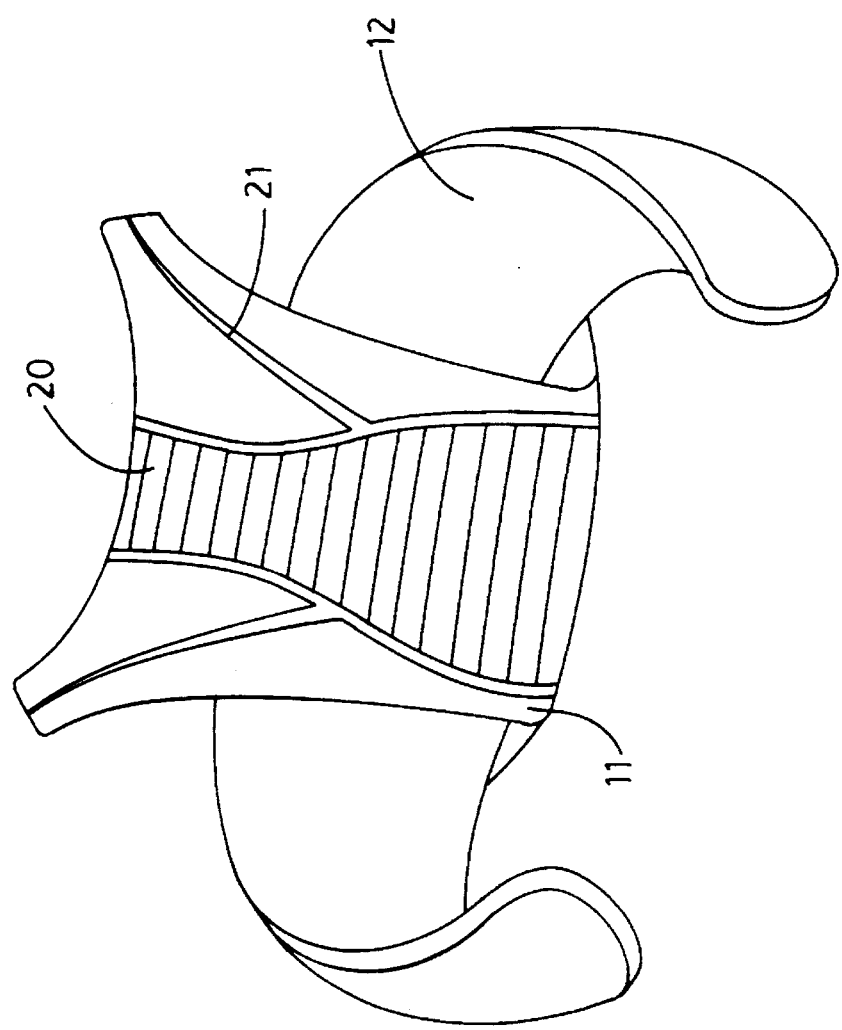
FIG. 5 is a perspective view of an alternative embodiment of the present invention illustrating a pre-molded version of the pad which includes the pocket (not shown) for receiving the inflatable bag (not shown).

In the alternative embodiment shown in FIG. 5, the foldable pad 11 is pre molded on at least one side to provide a series of horizontal grooves 20 and a pair of extending grooves 21. The opposite side (not shown in FIG. 5) is the same as that shown in FIG. 2 including the pocket 10 into which the inflatable bag 5 may be inserted. The padding between grooves 20 and 21 provides added comfort, and the grooves themselves provide channels for removal of perspiration and moisture away from the lumbar region of the wearer for additional comfort.

DESCRIPTION OF THE PREFERRED EMBODIMENTS

In the preferred embodiment, bag 5 of the present invention is made of a flexible airtight and watertight material, such as nylon, gortex® or plastic, although wood or other material may also be used. The corresponding waist belt 12 and pocket region 11 of pack 15 should be made of durable nylon or webbing with padding. The pocket closing means 13 should be a zipper, but could also be made of hook and loop fasteners (VELCRO®), snaps, buttons, or the like. Bag 5 is slided into pocket 10 and held in place by closing means 13.

The invention is designed so as to minimize any interference with the normal use of the waist belt, while at the same time providing available support and comfort by moving the weight of the pack off the users back through inflation of the bag.

The alternative embodiment shown in FIG. 5 improves comfort by providing additional padding as well as a means for removal of perspiration and moisture from the lumbar region of the wearer.

It is to be understood that variations and modifications of the present invention may be made without departing from the scope thereof. It is also to be understood that the present invention is not to be limited by the specific embodiments disclosed herein, but only in accordance with the appended claims when read in light of the foregoing specification.

I claim:

1. A backpacking device for providing relief from fatigue in the lumbar region of the back comprising a backpack including a closable waist belt attached near the bottom of the pack, said waist belt having an inside and an outside, a pad having a closable pocket therein, one end of said pad foldably attached to said waist belt adjacent to where said waist belt is attached to said pack, means for detachably connecting the opposite end of said pad to said pack, and an inflatable bag insertable into said pocket.

2. The device described in claim 1 above wherein one end of a hose is attached to said bag, and the other end of said hose is attached to a valve and hand pumping means.

3. The device described in claim 2 above wherein a closable release means is provided in said valve.

4. The device described in claim 1 above wherein a closing means is provided for said pocket in the form of a zipper.

5. The device described in claim 1 above wherein a closing means is provided for said pocket in the form of interengaging hooks and loops.

6. The device described in claim 1 above wherein said pad section is pre-molded and provided with a series of grooves for removal of moisture from the lumbar region.

7. A backpacking device for providing lumbar fatigue relief comprising the combination of a backpack having a waist belt with a closable pocket located therein and an inflatable bag insertable into said pocket.

8. The device described in claim 7 above wherein one end of a hose is attached to said bag, and the other end of said hose is attached to a valve and hand pumping means.

9. The device described in claim 8 above wherein said closable pocket is provided in a pad section that is foldably attached to said waist belt adjacent to where said waist belt is attached to said pack.

10. The device described in claim 9 above wherein a closing means is provided for said pocket in the form of a zipper.

11. The device described in claim 9 above wherein a closing means is provided for said pocket in the form of interengaging hooks and loops.

12. The device described in claim 9 above wherein said pad section is pre-molded and provided with a series of grooves for removal of moisture from the lumbar region.

13. The device described in claim 8 above wherein a closable release means is provided in said valve.

14. A device for providing relief from fatigue in the lumbar region of the back comprising an inflatable bag attached to a hose and air filling means, a waist belt attached to a backpack having a pad foldably attached thereto at a location between the ends of the belt, said pad having a closable pocket therein for receiving said bag, said pad also having a means for attachment to said backpack, wherein said closable pocket includes an opening through which to extend said hose when said pocket is closed.

15. The device described in claim 14 above wherein a closing means is provided in said pocket in the form of a zipper.

16. The device described in claim 14 above wherein a closing means is provided in said pocket in the form of interengaging hooks and loops.

17. In combination a backpack, waist belt, and inflatable bag for use in providing relief in the lumbar region of the back wherein one end of a pad is foldably attached to said waist belt at a location equidistant from either end of said belt, said waist belt is attached to said backpack, the opposite end of said pad is detachably connectable to said backpack, and said pad has a closable pocket therein for receiving said bag.

18. The device described in claim 17 above wherein said bag is attached to a hose and air filling means, and said closable pocket includes an opening through which to extend said hose when said pocket is closed.

19. The device described in claim 17 above wherein a closing means is provided in said pocket in the form of a zipper.

20. The device described in claim 17 above wherein a closing means is provided in said pocket in the form of interengaging hooks and loops.

* * * * *